United States Patent [19]

Sturtz

[11] Patent Number: 4,460,548
[45] Date of Patent: Jul. 17, 1984

[54] EXTRACTION OF URANIUM WITH DIPHOSPHONIC COMPOUNDS

[75] Inventor: Georges Sturtz, Brest, France

[73] Assignee: Societe Nationale Elf Aquitaine (Production), France

[21] Appl. No.: 166,363

[22] Filed: Jul. 7, 1980

[30] Foreign Application Priority Data

Jul. 9, 1979 [FR] France ............................... 79 17736

[51] Int. Cl.$^3$ .............................................. C01G 43/00
[52] U.S. Cl. ...................................... 423/10; 260/932
[58] Field of Search ..................... 423/8, 10; 210/634; 260/932; 252/184

[56] References Cited

U.S. PATENT DOCUMENTS

| | | | |
|---|---|---|---|
| 2,765,279 | 10/1956 | Nüsslein | 260/932 |
| 3,256,370 | 6/1966 | Fitch et al. | 260/932 |
| 3,471,552 | 10/1969 | Budnick | 260/932 |
| 3,534,125 | 10/1970 | Knollmueller | 260/932 |
| 3,743,688 | 7/1973 | Nicholson et al. | 260/932 |
| 3,993,728 | 11/1976 | Schulz | 423/10 |
| 4,105,741 | 8/1978 | Wiewiorowski et al. | 423/10 |

FOREIGN PATENT DOCUMENTS 410029 4/1972 U.S.S.R. .............................. 260/932

OTHER PUBLICATIONS

Hurst, "Solvent Extraction of Uranium from Wet Process Phosphoric Acid", ORNL-TM-2522, p. 39, (1969).

Primary Examiner—Edward A. Miller
Attorney, Agent, or Firm—Ostrolenk, Faber, Gerb & Soffen

[57] ABSTRACT

New diphosphonic acid diesters in which the two phosphorus atoms are bound by a hydrocarbon group while each of the two acid functions of the diphosphonate is esterified by a radical having at least three carbon atoms are suitable for various known uses of the different diphosphonates and in particular for the complexing of heavy metals; they are used in particular for the extraction of uranium and metals associated with it.

10 Claims, No Drawings

EXTRACTION OF URANIUM WITH DIPHOSPHONIC COMPOUNDS

This invention concerns a new group of diphosphonic compounds, in particular diphosphonic acid diesters, in which the two phosphorus atoms are connected by a hydrocarbon group. The invention also comprises a method of producing these new compounds.

Various phosphonates and diphosphonates are known in industry in which they find various uses. Thus, wetting agents, emulsifiers and plasticizers having a base of phosphonates are known in which the organic group directly bound to the phosphorus is ketalic, acetalic or dihydroxyl; such products, which can also be used as retardants of combustion for cellulose and different polymers are described in French Patent No. 1,459,049. Antioxidant phosphonates form the object of French Patent Publication No. 2,048,493, while diphosphonates are proposed as polymer antioxidants and stabilizers in accordance with French Publication No. 2,268,800. Polymeric phosphonates and diphosphonates form part of various resin compositions in accordance with U.S. Pat. No. 3,220,989 and French Publication No. 2,184,706. Furthermore, an entire range of pesticides having a base of sulfur phosphonates are available on the market, in particular under the brand name "Demephon". Another interesting application of certain diphosphonates is the complexing of heavy metals; this use as chelating agents is indicated, for instance, in U.S. Pat. No. 2,599,807 and U.S. Pat. No. 2,609,390. It is to be noted that in the derivatives of diphosphonic acids used up to the present time, the connection between the two phosphorus atoms is effected via oxygen and/or sulfur, which is the cause of a certain lack of stability of the compounds in question. In view of the very general usefulness of these compounds, it was of interest to seek more stable diphosphonates; this was the purpose of the work which led to the present invention.

The new partially esterified diphosphonic acids in accordance with the invention have the advantage of better stability than the corresponding compounds of the prior art. They are suitable for various known general uses of phosphonates; in particular they can be used as chelating agents for heavy metals and as agents for the extraction of certain metals such as uranium and metals associated with it, nickel and the like, from materials containing these metals.

These diphosphonic acids are characterized by the fact that the two phosphorus atoms which they contain are connected by a divalent hydrocarbon group each valence of which is exchanged with the phorphorus by means of a direct phosphorus-carbon bond, and that one of the two acid functions which each of the phosphorus atoms bears is esterified by a radical having at least two carbon atoms.

The new products in accordance with the application can be represented by the formula

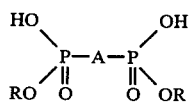

in which A designates a hydrocarbon group, which may in particular be aliphatic, cycloaliphatic, aryl or alkaryl, and R represents alkyl, cycloalkyl, alkenyl, aryl or alkaryl.

More particularly, the A groups are $C_1$ to $C_{18}$ and particularly $C_2$ to $C_6$ groups. These groups are, for instance, alkenyls such as $—CH_2—$, $—CH_2CH_2—$, $—CH_2CH_2CH_2—$,

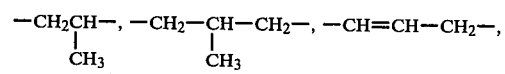

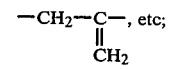

they may also consist of phenylene, possibly substituted, or of cyclopentyl or cyclohexenyl groups with or without substituent.

The radicals R are generally alkyls having at least two carbon atoms, generally $C_4$ to $C_{20}$ alkyls and particularly $C_6$ to $C_{18}$ alkyls. They may also be phenyls, tolyls, xylyls, ethyl-phenyls, propyl-phenyls, butyl-phenyls, diethyl-phenyls, dipropyl-phenyls, dibutyl-phenyls, hexyl-phenyls, dodecyl-phenyls, pentacyclo-hexyls, hexacyclo-hexyls or others, this enumeration being merely by way of illustration and not of limitation.

The diphosphonic acid diesters of the invention have variable physical properties and particularly melting and boiling points, depending on the nature of the groups A and R; it is therefore possible always to find within this series the compound appropriate for a given use by selecting the nature of these groups A and R accordingly.

The invention also comprises a process for the preparation of the new compounds described above. This process consists in transforming the corresponding tetramethyl diphosphonate by replacing, on each of the phosphorus atoms of the molecule, one $—OCH_3$ group by the desired $—OR$ group while the second $—OCH_3$ is hydrolyzed to $—OH$. In order to effect this transformation, the new process is carried out in three successive steps:

1—treatment of the starting compound (of formula II) by a weak base, preferably amine, so as to form a methyl diester disalt;
2—reaction of a halide of hydrocarbon radical R with the disalt to substitute the R for the cation of the base used;
3—hydrolysis of the two remaining $—OCH_3$.

These operations can be illustrated by the following equations (1) to (3) in one special method of operation:

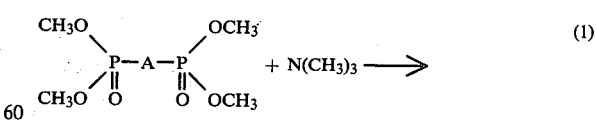

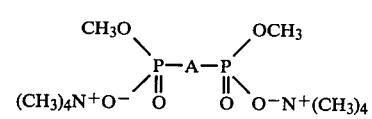

-continued salt IV + 2RBr ⟶ 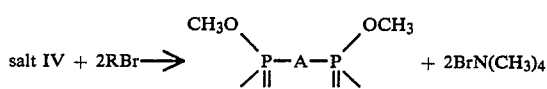 + 2BrN(CH₃)₄ (2)

V

Compound V + H₂O ⟶ 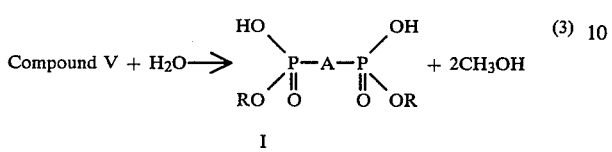 + 2CH₃OH (3)

I

Reaction (1) is carried out within an anhydrous solvent, for instance an alcohol, at a temperature of about 50° to 100° C., with agitation for several hours. The base used (III) should be of weak type, that is to say with an ion dissociation constant of not more than $10^{-3}$ and preferably between $10^{-4}$ and $10^{-6}$. Amines are particularly well-suited for this purpose and lead to quaternary ammonium disalts (IV). Thus, one can employ the methyl, ethyl, propyl, isopropyl, butyl, isobutyl, tert-butyl, pentyl and hexyl amines, the corresponding di- and tri-amines, benzyl amines, ethanolamines, etc. The trimethyl amine (III) which appears in reaction (1) described above and the dissociation constant of which is $5.27 \times 10^{-5}$ at 25° C. is particularly well-suited, both from a chemical standpoint and from an economic standpoint.

It is to be noted that the quaternary ammonium salts represented by formula (IV) are new chemical products which serve as intermediates in the process of the invention. They therefore from part of the invention. It has been possible to obtain them in good yields, namely 90% when A is —CH₂CH₂—

85% when A is —CH₃CH—
                    |
                    CH₃

90% when A is —CH₂—C—
                    ‖
                    CH₂

70% when A is —CH₂CH=CH—

In reaction (2), the tetramethyl ammonium salt (IV) collected at the end of step (1) is dissolved again in a solvent, preferably boiling between 50° and 100° C.; this solvent must, of course, be chemically inert with respect to the salt treated. Polar aprotic solvents are used, for instance dimethylformamide, dimethylsulfoxide, hexamethylphosphotriamide, acetonitrile, etc. To this solution there is added a slight excess of halide, particularly chloride or bromide of R, namely RBr in the example of reaction (2) above. Acetonitrile which boils at 81.6° C. is particularly well suited. It is heated under reflux for several hours, in general 4 to 10 hours, until the quaternary ammonium halide has precipitated. At the end, the mixed diester (V) is separated from its solution in the solvent used and is hydrolyzed in step (3).

Although reaction (3) is essentially a hydrolysis, it is preferably preceded by a reaction producing a metallic salt in which a cation, in particular, an alkali or alkaline earth metal replaces each of the —CH₃ present in the molecule (V). For this, this compound (V) is placed in solution in a suitable solvent which can at the same time dissolve a sufficient amount of an iodide, for instance Na or K iodide.

The sodium or potassium salt thus formed precipitates and it is then sufficient to wash it with acid in order to obtain the desired diphosphonic acid (I). Particularly favorable results are obtained with an acetone solution of NaI, which is refluxed for several hours with the mixed diester (V). The precipitate obtained is washed with acetone and then treated with hydrochloric acid in order to transform the sodium derivative into the acid (I).

With reference to the starting material for this process, that is to say the tetramethyl diphosphonate (II), it may be synthesized by one of the methods known per se. Thus, when A is, for instance, —CH₂CH₂ or

—CH₂CH—,
   |
   CH₃ dimethyl phosphite can be reacted with dimethyl vinyl phosphonate in the presence of sodium methylate as catalyst in methanol:

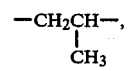

⟶

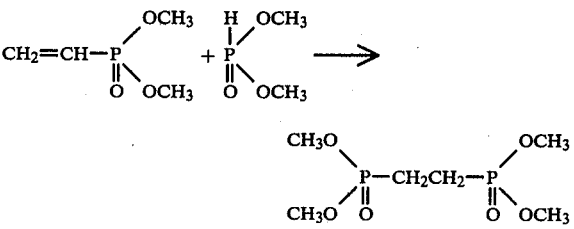

When A is an unsaturated aliphatic group, in particular

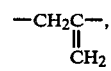

product (II) can be prepared by ABRUZOV isomerization between trimethyl phosphite and dichloro-2,3-propene.

The invention is illustrated by the following non-limitative examples.

EXAMPLE 1

Preparation of tetramethyl ammonium disalt (IV)

0.5 mol of tetramethyl diphosphonate of formula (II) in which A is the ethylene group —CH₂CH₂— is introduced into a 1 liter autoclave. 1.3 mol of trimethylamine, namely an excess of 30%, and 400 ml of dry methanol are added. The reaction takes place at 80° C. with agitation for 15 hours. After cooling, the methanol is expelled under reduced pressure and the crystals formed are collected; this product is recrystallized from acetone, which is then removed by filtration. After drying (yield: 90%) the NMR spectrum, recorded on a Jeol C 60 HL apparatus using tetramethyl silane as internal reference, led to the following results.

A =

-continued $$-CH_2-CH_2-\underset{a}{(CH_3)_4N^+O^-}-\underset{\underset{\underset{c}{CH_3O}}{|}}{\overset{\overset{O}{\|}}{P}}-\underset{b}{CH_2-CH_2}-\underset{\underset{\underset{c}{OCH_3}}{|}}{\overset{\overset{O}{\|}}{P}}-O^-\underset{a}{N^+(CH_3)_4}$$

EXAMPLE 2

Tetramethyl ammonium disalt (IV) in which A is the group $$-CH_2-\underset{\underset{CH_2}{\|}}{C}-$$

The operations are the same as in Example 1, applied to a diphosphonate of formula (II) in which A is the group indicated above.
The yield is 90% and the NMR spectrum indicates:

$$A = -CH_2-\underset{\underset{CH_2}{\|}}{C}-\;\underset{a}{(CH_3)_4N^+O^-}\underset{\underset{\underset{b}{CH_3O}}{/}}{\overset{\overset{O}{\|}}{P}}-\underset{c}{CH_2}-\underset{\underset{\underset{CH_2}{\|}}{d}}{C}-\underset{\underset{\underset{e}{OCH_3}}{\|\backslash}}{\overset{\|}{P}}\;\underset{a}{O^-N^+(CH_3)_4}$$

$\delta Ha = 3.275$ ppm singlet (24H),
$\delta Hb = 3.55$ ppm doublet (3H) JPHb = 0.5 Hz,
$\delta Hc =$ multiplet between 2.2 and 2.85 ppm (2H),
$\delta Hd =$ massive between 5.6 and 6.5 ppm (2H),
$\delta He = 3.65$ ppm doublet (3H) JPHe = 10.5 Hz.

EXAMPLE 3

In accordance with the technique of Examples 1 and 2, one starts from tetramethyl diphosphonate in which the A group is $-CH_2-CH=CH-$. The yield is 70%. The NMR data are $$A = -CH_2-CH=CH-\;\underset{a}{(CH_3)_4N^+O^-}\underset{\underset{\underset{b}{CH_3O}}{/}}{\overset{\overset{O}{\|}}{P}}-\underset{c}{CH_2}-\underset{d}{CH}=\underset{e}{CH}-\underset{\underset{\underset{f}{OCH_3}}{\|\backslash}}{\overset{\|}{P}}\;\underset{a}{O^-N^+(CH_3)_4}$$

$\delta Ha = 3.225$ ppm singlet (24H),
$\delta Hb = 3.52$ ppm doublet (3H) JPHb = 10.5 Hz,
$\delta Hc =$ massive between 2.4 and 3 ppm (2H),
$\delta Hd + He =$ massive between 5.4 ppm and 6.5 ppm (2H),
$\delta Hf = 3.55$ doublet (3H) JPHf = 10.5 Hz.

EXAMPLE 4

Transformation of tetramethyl ammonium disalt into mixed diphosphonate of formula (V).
The disalt is that of Example 2 in which A is $$-CH_2\underset{\underset{CH_2}{\|}}{C}=,$$

0.1 mol of the tetramethyl ammonium salt together with 0.21 mol of 2-ethyl-hexyl bromide $$\underset{C_2H_5}{\overset{C_4H_9}{\diagdown}}CH-CH_2Br$$

are introduced into a 500 ml three-neck flask provided with a magnetic agitator and a reflux condenser. The reaction is carried out in 250 ml of acetonitrile under reflux for 7 hours. A tetramethyl ammonium bromide precipitate is formed, which is separated by filtration under vacuum. The solvent is expelled by evaporation under reduced pressure so as to eliminate also a slight excess of bromine derivative. The data of the NMR spectrum are:

$$\underset{C_2H_5}{\overset{C_4H_9}{\diagdown}}\underset{a}{CH}-\underset{d}{CH_2}-O\underset{\underset{\underset{d}{CH_3O}}{/}}{\overset{\overset{O}{\|}}{P}}-\underset{b}{CH_2}-\underset{\underset{\underset{g}{CH_2}}{\|}}{C}-\underset{\underset{\underset{c}{OCH_3}}{\|\backslash}}{\overset{\|}{P}}\;O-\underset{f}{CH_2}\underset{a}{\overset{C_4H_9}{\diagup}}CH\underset{C_2H_5}{\diagdown}$$

TF = 258° C.

$\delta Ha =$ massive between 0.7 and 1.5 ppm (30H),
$\delta Hb =$ multiplet (6 lines) between 2.1 and 2.95 ppm (2H),
$\delta Hc = 3.675$ ppm doublet (3H) JPHc = 10.5 Hz,
$\delta Hd = 3.7$ ppm doublet (3H) JPHd = 10.5 Hz,
$\delta He + \delta Hf =$ massive centered at abt 3.85 ppm (4H),
$\delta Hg =$ multiplet included between 5.3 and 6.6 ppm (2H).

EXAMPLE 5

The manner of operation of Example 4 is applied to the transformation of the tetramethyl ammonium disalt of Example 2 into the mixed diphosphonate of formula (V) by the action of 2-ethyl hexyl bromide.

EXAMPLE 6

The transformation of the tetramethyl ammonium disalt obtained in Example 3 is effected in the same manner as in Example 4 by the action of 2-ethyl hexyl bromide.

EXAMPLE 7

The operations of Example 4 are repeated, the ethyl hexyl bromide being replaced by n-octyl bromide $C_8H_{17}Br$, which leads to the mixed diphosphonate (V) each of the R groups of which is a $-C_8H_{17}$ group.

EXAMPLE 8

One proceeds in the same manner as in Example 7, but the alkyl bromide employed is lauryl bromide $C_{12}H_{25}Br$.

EXAMPLE 9

The operations of Example 8 are carried out on the tetramethyl ammonium disalt obtained in Example 2.

EXAMPLE 10

The operations of Example 8 are carried out on the tetramethyl ammonium disalt obtained in accordance with Example 3.

EXAMPLE 11

In a series of separate preparations, the mixed diphosphonates of formula (V) obtained in Examples 4 to 10 were hydrolyzed.

The manner of operation comprises two stages: precipitation of a sodium salt of the diphosphonate and then transfer to the corresponding acid by treating said salt with hydrochloric acid. 0.1 mol of mixed diphosphonate (V) and 0.22 mol of NaI in 300 ml of dry acetone are introduced into a 1 liter round-bottom flask provided with a reflux condenser and a magnetic agitator. It is refluxed for 5 hours, which causes the appearance of a precipitate; the latter is filtered under vacuum and then washed several times with hot acetone, which leaves yellowish crystals. By agitation of these crystals with 10% aqueous hydrochloric acid, one obtains the desired diphosphonic acid diester of formula (I).

The final product thus obtained is in each case subjected to analysis by NMR and by infrared.

The data of the spectra obtained are as follows:

NMR $$\begin{array}{c} C_4H_9 \\ {}_e\diagdown \\ {}_{C_2H_5}\diagup \end{array} \overset{b}{CH}-CH_2-O-\overset{\overset{O}{\|}}{\underset{\underset{a}{OH}}{P}}-CH_2-CH_2-\overset{\overset{O}{\|}}{\underset{\underset{a}{OH}}{P}}-OCH_2-\overset{b}{CH}\begin{array}{c} \diagup C_4H_9 \\ {}_e \\ \diagdown C_2H_5 \\ {}_d \end{array}$$

(overall yield 80%)

2Ha = 1 spread peak at abt. 7.8 ppm
4Hb = 1 multiplet between 3.5 and 4.5 ppm
Hc + Hd + He = 1 multiplet between 0.8 and 2.1 ppm.

IR $\nu C-H$ 2920 cm$^{-1}$
$\nu P=O$ 1200 cm$^{-1}$
$\nu P-O-H$ 970 cm$^{-1}$
$\nu P-O-C$ 1030 cm$^{-1}$

NMR $$\begin{array}{c} C_4H_9 \\ {}_f\diagdown \\ {}_{C_2H_5}\diagup \end{array} \overset{c}{CH}-CH_2-O-\overset{\overset{O}{\|}}{\underset{\underset{a}{OH}}{P}}-\overset{b}{CH}=CH-CH_2-\overset{\overset{O}{\|}}{\underset{\underset{a}{OH}}{P}}-OCH_2-\overset{c}{CH}\begin{array}{c} \diagup C_4H_9 \\ {}_f \\ \diagdown C_2H_5 \\ {}_e \end{array}$$

Ha = 1 spread peak located between 7.4 and 8.0 ppm
Hb = 1 multiplet contained between 5.5 and 6.5 ppm
Hc = 1 multiplet between 3.3 and 4.0 ppm
Hd = 1 multiplet between 2.4 and 3.0 ppm
He + Hf = 1 multiplet between 0.8 and 1.6 ppm

IR $\nu C-H$ 2920 cm$^{-1}$
$\nu C=C$ 1630 cm$^{-1}$
$\nu P=O$ 1220 cm$^{-1}$
$\nu P-O-H$ 1000 cm$^{-1}$

RMN $$\begin{array}{c} C_4H_9 \\ {}_f\diagdown \\ {}_{C_2H_5}\diagup \end{array} \overset{c}{CH}-CH_2-O-\overset{\overset{O}{\|}}{\underset{\underset{a}{OH}}{P}}-\overset{d}{CH_2}-\overset{\overset{CH_2}{\|}}{\underset{\underset{b}{C}}{C}}-\overset{\overset{O}{\|}}{\underset{\underset{a}{OH}}{P}}-OCH_2-\overset{c}{CH}\begin{array}{c} \diagup C_4H_9 \\ {}_f \\ \diagdown C_2H_5 \\ {}_e \end{array}$$

Ha = 1 poorly resolved peak at 8.6 ppm
Hb = 1 multiplet between 5.5 ppm and 6.5 ppm
Hc = 1 multiplet between 3.1 ppm and 4.0 ppm
Hd = 1 multiplet between 2.2 ppm and 2.9 ppm
He + Hf = 1 multiplet between 0.7 ppm and 1.6 ppm The overall yield of this preparation is 82%.

| IR | $\nu C=C$ | 1630 cm$^{-1}$ | $\nu C-H$ | 2920 cm$^{-1}$ |
|---|---|---|---|---|
| | $\nu P=O$ | 1200 cm$^{-1}$ | $\nu P-OH$ | 970 cm$^{-1}$ |
| | $\nu P-O-C$ | 1020 cm$^{-1}$ | | |

Certain symmetric dialkyl-diphosphonic compounds in which A is in its preferred range ($C_2$ to $C_6$) have particularly interesting uranium-extracting properties. Those in which the two phosphorus atoms are separated by two carbon atoms are the most effective for the extraction of uranium and the metals associated with it. In this case, there is selected a radical R having a number of carbon atoms of between 6 and 18 and preferably between 8 and 14.

To the phosphoric solutions whose composition is indicated below, the compounds of the invention are added dissolved in an organic diluent such as petroleum distillation fractions, among which mention may be made of kerosene, dodecane and the product sold under the trademark SOLVESSO 200, or else dissolved in more polar solvents, particularly chlorinated solvents, such as, for instance, chloroform or trichlorethylene.

The concentration of the diester of the diphosphonic acid in accordance with the invention is 1 to 30% and preferably between 1 and 10% by weight, namely about 0.01 to 0.1 mol/liter.

The extraction process defined above applies particularly well to phosphoric solutions whose composition and pH are within the following limits:

| | Ordinary range | Preferred range |
|---|---|---|
| $P_2O_5$ | from 10 to 45% | from 25 to 35% |
| Ca | from 0 to saturation | from 0 to 2 g/L |
| Fe total | from 2 to 30 g/L | from 5 to 20 g/L |
| U | from 10 mg/L to saturation | above 10 mg/L |
| $SO_4^{--}$ | from 0 to 40 g/L | from 5 to 30 g/L |
| $F^-$ | from 0 to 40 g/L | from 0 to 20 g/L |
| Actinides and rare earth metals | from 0 to the limit of solubility | from 0 to 100 mg/L |
| pH | <2 | <1 |

The following non-limitative example is intended to enable those skilled in the art to determine the operating conditions which it is advisable to use in each particular case.

EXAMPLE 12

The tests were carried out with one volume of extractant organic phase to 10 volumes of aqueous phase. The extractant phase contained 30 g of reagent, that is to say of unpurified diphosphonate per liter of diluent (in the present case, kerosene).

The aqueous phase consisted of a sample of crude phosphoric acid of the following average composition:

U: 140 mg/L
Fe: 8 g/L
$SO_4$: 30 g/L
Ca: 1 g/L
Al: 3 g/L
F: 14 g/L
$SiO_2$: 8 g/L
$P_2O_5$: 400 g/L

Before extraction, the uranium was brought to valence IV by reduction by means of 5 g of metallic iron per liter of liquor to be reduced.

The extractions were effected in a single step by agitating the two phases for ten minutes at temperatures of 30° to 45° C.

The following table summarizes the results obtained with different diphosphonates of formula I, the R and A of which are indicated therein.

The $U^{IV}$ content of the initial aqueous solution is 140 mg/L. The $Fe^{III}$ content is 1900 mg/L for tests (1) to (3) and (5) and 800 mg/L for test (4).

The symbols $C_U$ and $C_{Fe}$ designate the final concentrations in mg/L in the spent aqueous solution, while $K_U$ and $K_{Fe}$ are the contents in mg/L of U and Fe respectively in the kerosene after extraction.

The ratio $K_U/C_U$ is the extraction coefficient.

|   |   | $C_U$ | $C_{Fe}$ | $K_U$ | $K_{Fe}$ | $K_U/C_U$ |
|---|---|---|---|---|---|---|
| (1) | R: dodecyl<br>A: 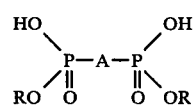 | 22 | 1410 | 1180 | 495 | 53.6 |
| (2) | R: octyl<br>A: —$CH_2$—$CH_2$— | 70 | — | 700 | 1200 | 10 |
| (3) | R: dodecyl<br>A: 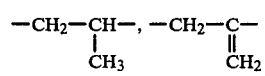 | 70 | — | 700 | 1050 | 10 |
| (4) | R: octyl<br>A: same as (3) | 78 | 200 | 620 | 605 | 7.95 |
| (5) | R: octyl<br>A: same as (1) | 5 | — | 1400 | 150 | 280 |

It is seen that the extraction of the U takes place very well, particularly when R is an octyl and A an allyl. In fact, test (5) leads to the very high extraction coefficient of 280.

I claim:

1. A method for the extraction of uranium from aqueous solution containing 10–45% by weight of phosphoric acid which comprises contacting said aqueous solution with a composition comprising an organic liquid containing 1 to 30% by weight of a diphosphonic diacid diester of the formula $$\begin{array}{c} HO \\ \diagdown \\ RO \end{array} P \begin{array}{c} \\ \diagup \\ O \end{array} -A- \begin{array}{c} \diagup OH \\ P \\ \diagdown OR \end{array}$$

in which A is a grouping selected from the group consisting of —$CH_2$—$CH_2$—,

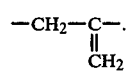

and —$CH_2$—CH=CH and R is a $C_6$ to $C_{18}$ alkyl.

2. The method of claim 1 wherein the organic liquid is selected from the group consisting of fractions of petroleum distillation, dodecane and chlorinated solvents.

3. The method of claim 1 wherein R is a $C_8$ to $C_{14}$ alkyl.

4. A method according to claim 1 wherein R is dodecyl and A is

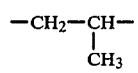

5. A method as claimed in claim 1 wherein R is octyl and A is —$CH_2$—$CH_2$—.

6. A method as claimed in claim 1 in which A is $$-CH_2-CH- \atop | \atop CH_3$$

and R is dodecyl or octyl.

7. A method as claimed in claim 1 wherein the organic liquid is kerosene.

8. A method as claimed in claim 1 in which the organic liquid contains between 1 and 10% by weight of the diphosphonic diacid diester.

9. The method of claim 1 wherein the aqueous solution is contacted with 1 volume of said composition to 10 volumes of said aqueous solution.

10. The method of claim 1 wherein said contacting is effected at temperatures of 30°–45° C. with agitation.